United States Patent
Seo et al.

(10) Patent No.: US 9,320,498 B2
(45) Date of Patent: Apr. 26, 2016

(54) TWINKLE ARTIFACT SUPPRESSION IN ULTRASOUND COLOR FLOW

(71) Applicants: Chi Hyung Seo, Sammamish, WA (US); King Yuen Wong, Issaquah, WA (US)

(72) Inventors: Chi Hyung Seo, Sammamish, WA (US); King Yuen Wong, Issaquah, WA (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 153 days.

(21) Appl. No.: 14/164,031

(22) Filed: Feb. 17, 2014

(65) Prior Publication Data

US 2015/0230777 A1    Aug. 20, 2015

(51) Int. Cl.
*A61B 8/08* (2006.01)
*A61B 8/06* (2006.01)

(52) U.S. Cl.
CPC ............... *A61B 8/5276* (2013.01); *A61B 8/488* (2013.01); *A61B 8/5269* (2013.01); *A61B 8/06* (2013.01); *A61B 8/5207* (2013.01)

(58) Field of Classification Search
CPC ........... A61B 8/00; A61B 8/06; A61B 8/5269
See application file for complete search history.

(56) References Cited

U.S. PATENT DOCUMENTS

2013/0336560 A1 * 12/2013 Wong .................. G01S 15/8981
382/131

OTHER PUBLICATIONS

T. Taso et al., "Correlation Study of the Strength of the Color Doppler Twinkling Artifact with the Roughness of the Reflecting Surface and the Doppler Angles," J Med Ultrasound 2004, vol. 12, No. 4, pp. 119-124.
J. Gao et al., "Flow turbulence or twinkling artifact? A primary observation on the intrarenal color Doppler sonography," Clinical Imaging 34, pp. 355-360, 2010.
A. Jamzad et al., "Simulation of the Twinkling Artifact in Color Flow Doppler Sonography: A Phase Noise Hypothesis Validation," 2011 IEEE International Conference on Signal and Image Processing Applications, pp. 22-27.
H. Kim et al., "Color Doppler Twinkling Artifacts in Various Conditions During Abdominal and Pelvic Sonography," J Ultrasound Med 2010, vol. 29, pp. 621-632.
H. R. Yazdi et al., "Twinkling Artifact in Patients with Urinary Stones," Iran J. Radiol 2010, vol. 7, No. 1, pp. 37-42.

* cited by examiner

*Primary Examiner* — Peter Luong

(57) ABSTRACT

Twinkle artifacts are suppressed in color flow. The color flow data itself, such as temporal decorrelation and spatial variance of the velocity and/or power, is used to identify the twinkle artifact. The aliased or high velocities caused by the twinkle artifact are suppressed, such as by reducing the velocity or by spatial filtering that adapts to the locations of the artifact. The powers caused by the twinkle artifact are suppressed.

20 Claims, 2 Drawing Sheets

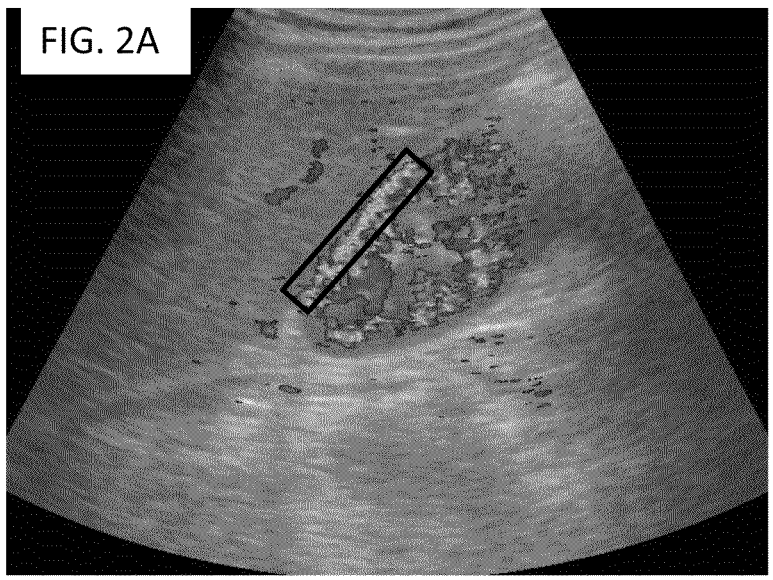
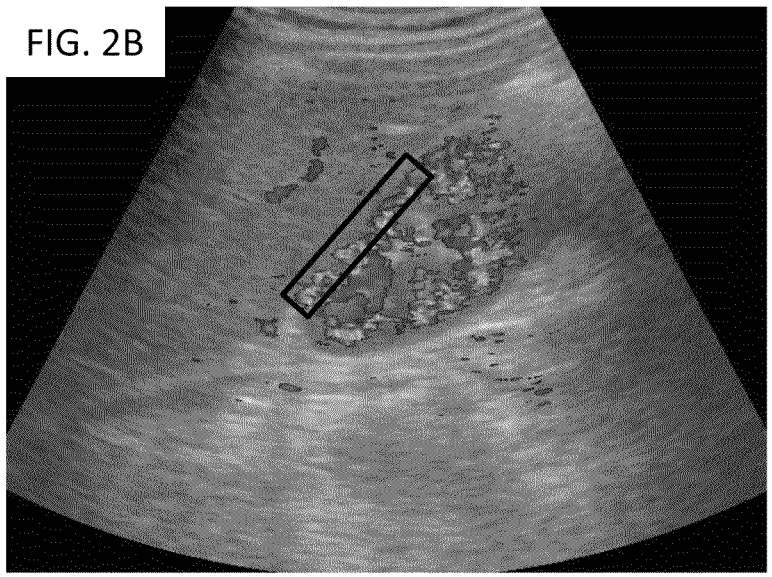

TWINKLE ARTIFACT SUPPRESSION IN ULTRASOUND COLOR FLOW

BACKGROUND

This present embodiments relate to color flow imaging. In particular, artifact suppression is provided for imaging tissue vascularity with color flow ultrasound imaging.

Color flow ultrasound imaging is commonly used to assess tissue vascularity. Doppler processing is used to estimate the velocities of blood in tissue. However, the Doppler signal is very sensitive to any types of motion and system noise or jitter, producing artifacts in the color flow image. Among these artifacts, twinkling artifacts (i.e., Christmas-like or phase noise) may result in misdiagnosis as the twinkling artifacts appear to be real, high or aliased flow. Twinkling artifacts are common and thought to be a result of surface roughness and system phase noise. Unlike normal blood flow, twinkling artifacts manifest as high velocity flow that is a function of anatomy and scan plane. Normally, gain or transmit power is adjusted to reduce the twinkling artifact. However, the change in gain or transmit power may result in a loss of sensitivity.

BRIEF SUMMARY

By way of introduction, the preferred embodiments described below include a method, system, computer readable medium, and instructions for twinkle artifact suppression in color flow. The color flow data itself, such as temporal decorrelation and spatial variance of the velocity, and temporal correlation of power (e.g., artifact strength) are used to identify the twinkle artifact. The aliased or high velocities caused by the twinkle artifact are suppressed, such as by reducing the velocity or by spatial filtering that adapts to the locations of the artifact.

In a first aspect, a method is provided for twinkle artifact suppression in color flow. Color flow ultrasound data representing a patient is acquired. A twinkle artifact represented in the color flow ultrasound data is detected from the color flow ultrasound data. The detection is a function of a decorrelation over time and spatial variance. The twinkle artifact is suppressed in the color flow ultrasound data. A color flow image is generated with the color flow ultrasound data after the suppressing.

In a second aspect, a non-transitory computer readable storage medium has stored therein data representing instructions executable by a programmed processor for twinkle artifact suppression in color flow. The storage medium includes instructions for scanning a plurality of locations with ultrasound, estimating velocities and powers for each of the locations at different times, correlating the velocities and powers from the different times for each of the locations, calculating spatial variance of at least some of the velocities for a first one of the different times, altering the velocities and powers for the locations based on results from the correlating and the spatial variance, and generating a velocity image with the velocities, including altered velocities resulting from the altering.

In a third aspect, a system is provided for twinkle artifact suppression in color flow. A transducer and beamformer are for scanning a scan region. A Doppler estimator is configured to estimate velocities and powers representing samples of a scan region at different times. A processor is configured to identify twinkling artifacts in the velocities and powers using spatial and temporal characteristics of the velocities and powers and to change the velocities and powers of the twinkling artifacts.

The present invention is defined by the following claims, and nothing in this section should be taken as a limitation on those claims. Further aspects and advantages of the invention are discussed below in conjunction with the preferred embodiments.

BRIEF DESCRIPTION OF THE DRAWINGS

The components and the figures are not necessarily to scale, emphasis instead being placed upon illustrating the principles of the invention. Moreover, in the figures, like reference numerals designate corresponding parts throughout the different views.

FIGS. 2A and 2B are example images without and with twinkle artifact suppression, respectively.

DETAILED DESCRIPTION OF THE DRAWINGS AND PRESENTLY PREFERRED EMBODIMENTS

A color flow artifact is suppressed in an ultrasound system. The artifact is first characterized by examining temporal and spatial domains. Information in the imaging data itself is used to reduce or eliminate the artifact. The main attributes of the twinkle artifact is high decorrelation between frames in the velocity domain and high temporal correlation of artifact strength in the power domain. Further, spatial correlation may be used to create a statistical mean and/or variance map. Based on any combination of these attributes, thresholding is employed to segment and suppress the artifacts. The twinkle artifact is reduced or eliminated without affecting sensitivity.

In one embodiment, twinkling artifacts are identified using their spatial and temporal correlation and randomness of velocity values. A filter calculates the spatial and temporal statistics of the flow image pixels and their velocities. Thresholding determines whether a given area of the flow image contains the artifacts or not. A filter removes flow pixels in the areas where the presence of artifacts are detected. The filter has a spatial and temporal response that adapts to the severity of artifacts with the goal to remove artifacts while leaving most legitimate flow pixels unaltered or altered less.

Figure 1:
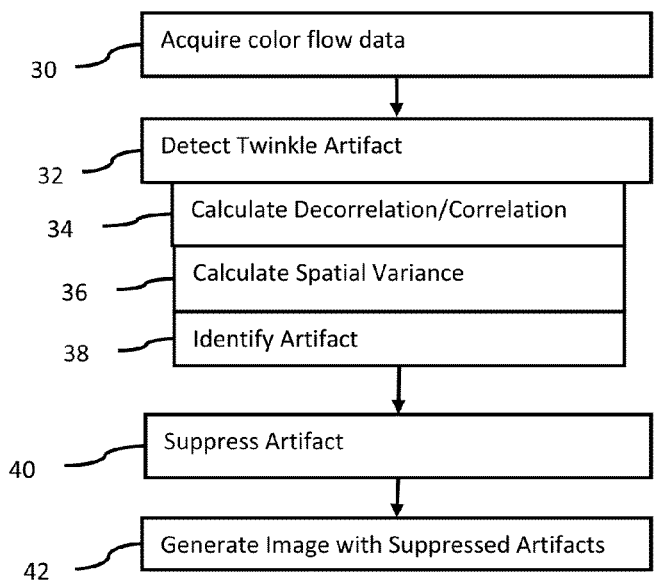
FIG. 1 is a flow chart of one embodiment of a method for twinkle artifact suppression in color flow.

FIG. 1 shows a method for twinkle artifact suppression in color flow. The method is performed by the system 10 of FIG. 3, the processor 24, or a different system, filter, and/or processor. The acts of FIG. 1 are performed in the order shown or a different order. Additional, different or fewer acts than shown in FIG. 1 may be used. For example, an act for calculating a statistical mean or other temporal and/or spatial statistics of the color flow data is provided to detect the artifact. In another example, an image is not generated in act 42, and the data with the suppressed artifact is instead stored or used for calculating a value (e.g., average flow velocity).

In act 30, color flow or flow ultrasound data is acquired. Color flow data includes estimates of velocity, energy (e.g., power), and/or variance. In one embodiment, at least velocity is estimated. To estimate the color flow, data representing blood, fluid, or flow of the patient is acquired.

The color flow data is acquired by transfer over a network, loading from memory, and/or by scanning a patient. For transfer or loading, data previously acquired by scanning is acquired. In one embodiment using an ultrasound system, a patient or region is scanned in real-time with the imaging. The scanned region is an interior of an object, such as the patient. The scan is of a volume, plane, or line region. Scanning a plane provides data representing different locations or samples of the plane. The data representing the region is formed from spatial sampling of the object. The spatial samples are for locations distributed in an acoustic sampling grid.

Spatial samples along one or more scan lines are received. Where the transmit beam insonifies just one receive scan line, then samples along that scan line are received. Where the transmit beam insonifies multiple scan lines, then samples along the multiple scan lines are received. To generate the samples for different receive beams, parallel receive beamformation is performed so that the different receive beams are sampled at a same time. For example, a system may be capable of forming two or more, tens or hundreds of receive beams in parallel. Alternatively, signals received from the elements are stored and sequentially processed. Spatial samples are acquired for a plurality of receive lines in response to one and/or in response to sequential transmit beams.

The scanning may be performed a plurality of times to cover the region. The acts are repeated to scan different portions of the region of interest. Alternatively, performing once acquires the data for the entire region of interest.

The complete region of interest is scanned multiple times at different times. Scanning at different times acquires spatial samples associated with flow or motion. Any now known or later developed pulse sequences may be used. A sequence of at least two (flow sample count) transmissions is provided along each scan line. Any pulse repetition frequency, flow sample count, and pulse repetition interval may be used. The echo responses to the transmissions of the sequence are used to estimate velocity, energy (power), and/or variance at a given time. The transmissions along one line(s) may be interleaved with transmissions along another line(s). With or without interleaving, the spatial samples for a given time are acquired using transmissions from different times. The estimates from different scan lines may be acquired sequentially, but rapidly enough to represent a same time from a user perspective. Multiple scans are performed to acquire estimates for different times.

The received spatial samples may be clutter filtered. The clutter filtering is of signals in the pulse sequence for estimating motion at a given time. A given signal may be used for estimates representing different times, such as associated with a moving window for clutter filtering and estimation. Different filter outputs are used to estimate motion for a location at different times.

Color flow data is generated from the spatial samples. Any flow data may be generated, such as velocity, energy (power), and/or variance. Doppler processing, such as autocorrelation, may be used. In other embodiments, temporal correlation may be used. Another process may be used to estimate the flow data. Color Doppler parameter values (e.g., velocity, energy, or variance values) are estimated from the spatial samples acquired at different times. "Color" is used to distinguish from spectral Doppler imaging, where the power spectrum for a range gate is estimated. The change in frequency between two samples for the same location at different times indicates the velocity. A sequence of more than two samples may be used to estimate the color Doppler parameter values. Estimates are formed for different groupings of received signals, such as completely separate or independent groupings or overlapping groupings. The estimates for each grouping represent the spatial location at a given time.

The estimation is performed for the different sampled spatial locations. For example, velocities for the different locations in a plane are estimated from echoes responsive to the scanning. Multiple frames of flow data may be acquired to represent the region of interest at different times, respectively.

The estimates may be thresholded. Thresholds are applied to the velocities and powers. For example, a low velocity threshold is applied. Velocities below the threshold are removed or set to another value, such as zero. As another example, where the energy is below a threshold, the velocity value for the same spatial location is removed or set to another value, such as zero. Alternatively, the estimated velocities are used without thresholding.

In act 32, the twinkle artifact represented in the color flow ultrasound data is detected. FIG. 2A shows a color flow image of a kidney. The color flow is velocity of blood to show vascularity in the kidney. The velocity scale is mapped to yellow for high positive velocities and light blue for high negative velocities. A box graphic that is not presented in the image displayed to the user is provided to show a region associated with the twinkle artifact. The box shows a general region where high velocities occur, looking like a vessel. However, these high velocities are due to the twinkling artifact, such as due to phase variation from jittering. The artifact causes aliasing. Others of the velocities mapped to colors show actual flow velocity and are desired, including in the region with the artifact.

The artifact is detected by the characteristics of the artifact reflected in the estimated velocities and/or powers. The velocities and/or powers themselves are used to detect the twinkle artifact. Any one or more attribute may be used. FIG. 1 shows detection of the temporal decorrelation and spatial variance of the velocities and temporal correlation of the powers (acts 34 and 36) from the color flow data. Other characteristics instead of or in addition to decorrelation and spatial variance may be used, such as statistical mean. Temporal decorrelation and/or spatial variance may not be used in other embodiments.

In one embodiment of act 34, the decorrelation over time is detected. Any correlation or similarity measure may be used. In one embodiment, a mathematical decorrelation is calculated from the sequence of samples over time. In another embodiment, a mere difference or average difference is calculated. The amount of difference over time is calculated.

The decorrelation is calculated separately for each sample location (e.g., scan sample or image pixel location). A sequence of samples for a given location is used to measure the variance over time for that location. In other embodiments, the locations are grouped and the decorrelation is over time for the grouped sub-region, such as measuring a cross-correlation between spatially distributed sets of color data from different times.

The amount of decorrelation (or amount of correlation) over time for each location or group of locations is calculated. Any range of times may be used, such as a moving window of pairs of frames or all frames during a heart cycle or part of a heart cycle. For a moving window, the artifact suppression and corresponding detection is repeated for each new frame of color flow data. The result is a decorrelation value or the inverse correlation value for each location at each time represented by velocity or other color flow data. The decorrelation represents a temporal change of the color flow data. Since the twinkle artifact twinkles or varies substantially over time, the locations associated with higher frequency variation than other locations are identified from the decorrelation or lack of correlation.

The decorrelation, or the inverse, are compared to a threshold to indicate whether the location is or may be associated with the twinkle artifact. Any threshold level may be used. The threshold may depend on system settings, the transducer being used, and/or the application (e.g., organ being imaged). For example, the threshold is 0.4 for the kidney application of FIG. 2A. If the decorrelation is above, or at or above the threshold, then the location may be or is associated with twinkle.

In one embodiment, the decorrelations for the different locations are used with other attributes to find the twinkle artifact. In other embodiments, the decorrelation attribute is used without other attributes. In yet another embodiment, the decorrelation attribute is used for masking in the calculation of other attributes.

As an alternative to velocity decorrelation or an additional attribute for masking or detection of the twinkle artifact, temporal correlations in powers is used. The amount of temporal correlation in power for each location is thresholded to identify whether that location is associated with a twinkle artifact. Like velocity correlation, any range of times or other filtering characteristics may be used for calculating the power correlation over time. The correlation of power may be expressed as a decorrelation of power.

In act 36, the spatial variance is calculated. The spatial variance is calculated as a statistical correlation across locations in a frame of color flow data for a given time. As a given frame of color flow data is estimated or acquired, the spatial variance is calculated.

In one embodiment, the locations are divided into separate or non-overlapping sub-regions. For example, a linear scan region is divided into a plurality of sub-rectangles. As another example, a sector or Vector® scan region is divided into a plurality of sub-sector or Vector® shapes (e.g., pie shaped sub-regions). The spatial variance is calculated separately for each sub-region. Any size sub-regions may be used, such as 5 beam (azimuth spacing) by 30 axial sample sub-regions for a sector or Vector® scan in the acoustic sample space. Each sub-region includes multiple locations for which color flow data is acquired. In alternative embodiments, a moving window approach is used where the spatial variance is calculated for a kernel region within or defined by the window centered over a given location. By moving the window, a spatial variance for each location is determined.

The decorrelation may be used to mask for the spatial variation calculation. Within a given window or sub-region for spatial variance calculation, only the color flow data for locations that may be twinkle artifact are used. Just the color flow data associated with decorrelation above the threshold (or correlation below the threshold) is used for calculating the spatial variance. Color flow data for other locations within the window or sub-region are not used. The locations associated with power correlation may also be used. Only locations with both decorrelation of velocity and correlation of power are used for spatial variation calculation. In other embodiments, locations associated with one or the other are used. Alternatively, all of the velocities or other color flow data within each window or sub-region are used to calculate the spatial variance (i.e., masking based on decorrelation is not used).

Other attributes may be calculated. For example, a statistical mean is calculated. Using the same or different sub-regions, a mean of the color flow data is calculated. The mean may be of the decorrelated color flow data only or all of the color flow data (i.e., with or without the masking based on decorrelation). As another example, a difference in means between velocities of the decorrelated and non-decorrelated locations in a sub-region is determined.

In act 38, the location or locations of the twinkle artifact are identified. One or more of the attributes are used to locate the artifact. For example, the velocity decorrelation results, power correlation results, and the spatial variance are used. As another example, the spatial variance for locations associated with the decorrelation is used.

In one embodiment, the attributes are thresholded. Other functions may be used, such as weighting the attributes for each location, combining the weighted attributes, and thresholding the result. In one embodiment, separate thresholds are applied to the values of each attribute. For the decorrelation, the same or different threshold used for masking the spatial variance calculation is used. For the spatial variance, another threshold is used. For any location within a sub-region, the spatial variance for that sub-region is used as the spatial variance value. If the both attributes for a given location satisfy the respective thresholds (e.g., both above the thresholds), then the color flow data for that location includes the artifact. The artifact likely has high temporal decorrelation in the velocities, high temporal correlation in the powers, and high spatial variation in the velocities. In another example, the location and corresponding color flow data are not identified as a twinkle artifact unless the statistical mean is below or equal to or below a mean threshold.

Any combination of above, below, or equal to thresholds for the different attributes may be used. All, most, or particular combinations of attributes are used to indicate the color flow data of a location as including or not including the artifact. For example, all of the decorrelation and spatial variance or all of the spatial variance, decorrelation, and statistical mean indicate artifact or the color flow data is considered to not include the artifact. As another example, all of the velocity decorrelation, power correlation, and spatial variance of velocity are satisfied to identify the artifact. If one of the attributes fails the threshold test, then the location and corresponding color flow data is identified as not being the twinkle artifact.

In act 40, the twinkle artifact in the color flow ultrasound data is suppressed. The color flow data is altered. The data after estimating and prior to mapping to color (e.g., estimated velocities) is altered. Alternatively, the mapped colors for the image are altered. In other embodiments, the mapping function for mapping from the data to the display pixels is altered to change the color flow ultrasound data.

The altering is performed for the locations identified as including twinkle artifacts. The color flow data for other locations is not altered, at least as part of the suppression of the twinkle artifact. In other embodiments, the color flow data for other locations may be altered, but have less of a change or a lesser magnitude of change than the color flow data for the locations that have the artifact.

Any alteration may be used. For example, the velocities and/or the powers for the artifact locations are set to an average of non-artifact velocities and/or powers with surrounding regions. As another example, the artifact velocities and/or the powers are set to a standard or pre-determined value. The velocity and/or powers of a nearest neighbor that does not include an artifact may be used. Interpolation or other approaches may be used to alter the color flow data by replacement.

In one embodiment, a spatial filter is used. The locations corresponding to the artifact are used to create a mask. Lower weights, such as zero, are set for the locations corresponding to the twinkle artifact. Higher weights, such as one, are set for other locations with non-artifact color flow data. The mask may then be spatially low-pass filtered so that other weights result. The higher weights are decreased, and the lower weights are increased. Where the lower weights are surrounded by lower rates, the lower rates may stay at the initial value. The weights are then applied to the color flow data. Since the lower weights are applied to the color flow data for the artifact locations, the velocities or other color flow data for those artifact locations are reduced more than for the non-artifact locations (e.g., 0.1×100=10 for artifact, reducing by 90 and 0.9×100=90 for non-artifact, reducing by 10). The weighting is applied by multiplication, but other functions may be used. Where a weight is zero, the color flow data is set to zero. B-mode data may be used for the image at such locations.

Power may be used to create a mask for suppression of the artifact in velocity and/or power data. Power values are temporally filtered. Filtered power acts as a mask that seeks out the artifacts, and the inverse mask may be used to attenuate the original power values accordingly. The severity of the artifacts may then be used to adjust the amount of filtering which will in turn suppress. At the same time, the velocity of the original flow image may also be reduced according to the attenuating values obtained by temporarily filtered power.

In act 42, a color flow image is generated. The color flow data after the suppression of the artifact is used to create a color image. For suppression of velocities or other color flow data prior to color mapping, the altered color flow data is mapped to the display values. For suppression of the velocities or other color flow data as mapped to colors, the altered colors are used as the display values. For velocity imaging, the velocity image includes velocities that have been altered to remove or reduce the twinkling artifact. Fewer of the pixels are mapped to the high or highest range of colors as compared to mapping without the suppression alteration.

The image may include other information. For example, the image is an overlay of the color flow data with B-mode data. For non-tissue locations or locations associated with sufficient flow, the color flow data (e.g., velocities) are used to determine a color to display. For tissue locations or low/no flow locations, the B-mode data is used.

FIG. 2B shows an example color flow image of velocities generated with suppression of the twinkling artifact. Using the spatial variance and decorrelation attributes where decorrelation masks the spatial variance calculation, the twinkling artifact is reduced or removed as compared to FIG. 2A by spatially filtering 0 and 1 weights of a mask. The same base velocities are used for both FIGS. 2A and 2B. In the rectangular region of FIG. 2B, fewer of the highest velocities (e.g., yellow in this mapping example) are shown. Some of the velocities are removed, resulting in a display of B-mode data. The suppression results in the flow region looking less like a vessel and more like tissue with vasculature as expected for the kidney.

Relative terminology, such as associated with amounts of altering, indicates a difference between values. For example, lower and higher alterations are magnitudes with relative difference, rather than absolutes. Different imaging situations may have different values, based on experimentation, dynamic range, imaging system, and/or user preference. The actual values may be any value.

Figure 3:
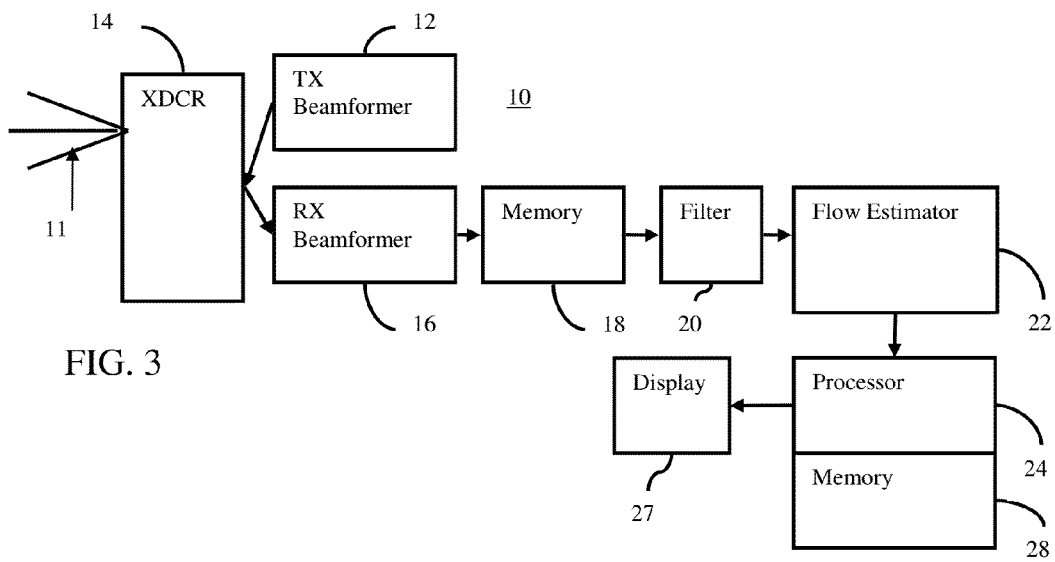
FIG. 3 is a block diagram of one embodiment of a system for twinkle artifact suppression in color flow.

FIG. 3 shows one embodiment of a system 10 for twinkle artifact suppression in color flow. The system 10 includes a transmit beamformer 12, a transducer 14, a receive beamformer 16, a memory 18, a filter 20, a flow estimator 22, a memory 28, a processor 24, and a display 27. Additional, different or fewer components may be provided. For example, the system includes a B-mode detector. As another example, the flow estimator 22 and processor 24 are provided without the front-end components, such as the transmit and receive beamformers 12, 16. In one embodiment, the system 10 is a medical diagnostic ultrasound system. In an alternative embodiment, the system 10 is a computer or workstation. In yet another embodiment, the flow estimator 22 is part of a medical diagnostic ultrasound system or other medical imaging system, and the processor 24 is part of a separate workstation or remote system.

The transducer 14 is an array of a plurality of elements. The elements are piezoelectric or capacitive membrane elements. The array is configured as a one-dimensional array, a two-dimensional array, a 1.5 D array, a 1.25 D array, a 1.75 D array, an annular array, a multidimensional array, a wobbler array, combinations thereof, or any other now known or later developed array. The transducer elements transduce between acoustic and electric energies. The transducer 14 connects with the transmit beamformer 12 and the receive beamformer 16 through a transmit/receive switch, but separate connections may be used in other embodiments.

The transmit and receive beamformers 12, 16 are a beamformer for scanning with the transducer 14. The transmit beamformer 12, using the transducer 14, transmits one or more beams to scan a region. Vector®, sector, linear or other scan formats may be used. The receive lines and/or transmit beams are distributed in the scan region. The receive beamformer 16 samples the receive beams at different depths. Sampling the same location at different times obtains a sequence for flow estimation.

In one embodiment, the transmit beamformer 12 is a processor, delay, filter, waveform generator, memory, phase rotator, digital-to-analog converter, amplifier, combinations thereof or any other now known or later developed transmit beamformer components. In one embodiment, the transmit beamformer 12 digitally generates envelope samples. Using filtering, delays, phase rotation, digital-to-analog conversion and amplification, the desired transmit waveform is generated. Other waveform generators may be used, such as switching pulsers or waveform memories.

The transmit beamformer 12 is configured as a plurality of channels for generating electrical signals of a transmit waveform for each element of a transmit aperture on the transducer 14. The waveforms are unipolar, bipolar, stepped, sinusoidal or other waveforms of a desired center frequency or frequency band with one, multiple or fractional number of cycles. The waveforms have relative delay and/or phasing and amplitude for focusing the acoustic energy. The transmit beamformer 12 includes a controller for altering an aperture (e.g. the number of active elements), an apodization profile (e.g., type or center of mass) across the plurality of channels, a delay profile across the plurality of channels, a phase profile across the plurality of channels, center frequency, frequency band, waveform shape, number of cycles and combinations thereof. A transmit beam focus is generated based on these beamforming parameters.

The receive beamformer 16 is a preamplifier, filter, phase rotator, delay, summer, base band filter, processor, buffers, memory, combinations thereof or other now known or later developed receive beamformer components. The receive beamformer 16 is configured into a plurality of channels for receiving electrical signals representing echoes or acoustic energy impinging on the transducer 14. A channel from each of the elements of the receive aperture within the transducer 14 connects to an amplifier and/or delay. An analog-to-digital converter digitizes the amplified echo signal. The digital radio frequency received data is demodulated to a base band frequency. Any receive delays, such as dynamic receive delays, and/or phase rotations are then applied by the amplifier and/or delay. A digital or analog summer combines data from different channels of the receive aperture to form one or a plurality of receive beams. The summer is a single summer or cascaded summer. In one embodiment, the beamform summer is configured to sum in-phase and quadrature channel data in a complex manner such that phase information is maintained for the formed beam. Alternatively, the beamform summer sums data amplitudes or intensities without maintaining the phase information.

The receive beamformer 16 is operable to form receive beams in response to the transmit beams. For example, the receive beamformer 16 receives one, two, or more receive beams in response to each transmit beam. The receive beams are collinear, parallel and offset or nonparallel with the corresponding transmit beams. The receive beamformer 16 outputs spatial samples representing different spatial locations of a scanned region. Once the channel data is beamformed or otherwise combined to represent spatial locations along the scan lines 11, the data is converted from the channel domain to the image data domain. The phase rotators, delays, and/or summers may be repeated for parallel receive beamformation. One or more of the parallel receive beamformers may share parts of channels, such as sharing initial amplification.

For imaging motion, such as tissue motion or fluid velocity, multiple transmissions and corresponding receptions are performed for each of a plurality of substantially same spatial locations. Phase changes between the different receive events for each given location indicate the velocity of the tissue or fluid. A velocity sample group corresponds to multiple transmissions for each of a plurality of scan lines 11. The velocity sample count is the number of times a substantially same spatial location, such as a scan line 11, is scanned within a velocity sample group. The transmissions for different scan lines 11, different velocity sample groupings or different types of imaging may be interleaved. The amount of time between transmissions to a substantially same scan line 11 within the velocity sample count is the pulse repetition interval or pulse repetition frequency. Pulse repetition interval is used herein, but includes the pulse repetition frequency.

The memory 18 is video random access memory, random access memory, removable media (e.g. diskette or compact disc), hard drive, database, corner turning memory or other memory device for storing data or video information. In one embodiment, the memory 18 is a corner turning memory of a motion parameter estimation path. The memory 18 is configured to store signals responsive to multiple transmissions along a substantially same scan line. The memory 22 is configured to store ultrasound data formatted in an acoustic grid, a Cartesian grid, both a Cartesian coordinate grid and an acoustic grid, or ultrasound data representing a volume in a 3D grid.

The filter 20 is a clutter filter, finite impulse response filter, infinite impulse response filter, analog filter, digital filter, combinations thereof or other now known or later developed filter. In one embodiment, the filter 20 includes a mixer to shift signals to baseband and a programmable low pass filter response for removing or minimizing information at frequencies away from the baseband. In other embodiments, the filter 20 is a low pass, high pass or band pass filter. The filter 20 isolates velocity information from slower moving tissue as opposed to fluids or alternatively reduces the influence of data from tissue while maintaining velocity information from fluids. The filter 20 has a set response or may be programmed, such as altering operation as a function of signal feedback or other adaptive process. In yet another embodiment, the memory 18 and/or the filter 20 are part of the flow estimator 22.

The flow estimator 22 is a Doppler processor or cross-correlation processor for estimating the color flow data. In alternative embodiments, another device now known or later developed for estimating velocity, power (e.g., energy), and/or variance from any or various input data may be provided. The flow estimator 22 receives a plurality of signals associated with a substantially same location at different times and estimates a Doppler shift frequency, based on a change or an average change in phase between consecutive signals from the same location. Velocity is calculated from the Doppler shift frequency. Alternatively, the Doppler shift frequency is used as a velocity. The power and variance may also be calculated.

Color flow data (e.g., velocity, power, or variance) is estimated for spatial locations in the scan region from the beamformed scan samples. For example, the flow data represents a plurality of different locations in a plane.

The flow estimator 22 may apply one or more thresholds to identify sufficient motion information. For example, velocity and/or power thresholding for identifying velocities is used. In alternative embodiments, a separate processor or filter applies thresholds.

The flow estimator 22 outputs frames of data representing the scan region at different times. The beamformed samples for a given flow sample count are used to estimate for a time. A moving window with overlap of the data is used to estimate for other times. Velocities for each location at different times are output.

The processor 24 is a digital signal processor, a general processor, an application specific integrated circuit, field programmable gate array, control processor, digital circuitry, analog circuitry, graphics processing unit, combinations thereof or other now known or later developed device for implementing calculations, algorithms, programming or other functions. The processor 24 operates pursuant to instruction provided in the memory 28, or a different memory for twinkle artifact suppression in medical diagnostic ultrasound.

The processor 24 receives color flow data from the flow estimator 22, the memory 28, and/or another source. In one embodiment, the processor 24 implements one or more of the algorithms, acts, steps, functions, methods or processes discussed herein, by processing the data and/or controlling operation of other components of the system 10. Additional or multiple processors may be used to implement various aspects of the algorithms.

The processor 24 is configured by software and/or hardware to identify twinkling artifacts in the velocities. Spatial and/or temporal characteristics of the velocities and powers are calculated. Any spatial or temporal characteristics may be used. For example, the temporal characteristic is calculated as a degree of correlation and the spatial characteristic as a spatial variance. The decorrelation may be a simple difference between values from two different times for a same location. The attributes are calculated for each location. Some locations may share a same calculation, such as the spatial characteristic being determined for a region or multiple locations.

The processor 24 identifies the twinkling artifacts where the decorrelation is above a first threshold and the spatial variance is above a second threshold. Additional, different, or less information may be used to identify the artifacts, such as the processor 24 calculating and applying a threshold to a statistical mean. The thresholding may include equal to or not include equal to. Where the decorrelation is expressed as the inverse or correlation, the twinkling artifact may be identified, at least in part, based on the temporal characteristic being below the threshold.

The processor 24 is configured to change the velocities and powers of the twinkling artifacts. The processor 24 assigns new velocities and new powers, reduces the velocities and powers, removes the velocities and/or otherwise alters the magnitude of the velocities. In one embodiment, the velocities are altered as a function of a severity of the artifacts as indicated by the spatial and temporal characteristics. More highly temporally decorrelated and/or greater variance velocities are reduced more than less highly decorrelated and/or less great variance. For example, the power values are temporally filtered. Artifact strength tends to stay correlated while the real flow gets decorrelated over time due to variation in the cardiac cycle. This filtered power acts as a mask that seeks out the artifacts and the inverse mask may be used to attenuate the original power values accordingly. The severity of the artifacts may then be used to adjust the amount of filtering which will in turn suppress. At the same time, the velocity of the original flow image may also be reduced according to the attenuating values obtained by temporarily filtered power. Alternatively, the change is by a set amount regardless of the severity of the artifacts.

The processor 24 is configured to reduce the velocities and/or powers of the twinkling artifacts more than reducing of the velocities not of the twinkling artifacts. This relative change suppresses the twinkling artifacts in the velocity image.

The memory 28 is video random access memory, random access memory, removable media (e.g. diskette or compact disc), hard drive, database, or other memory device for storing color flow data. The stored data is in a polar or Cartesian coordinate format. The memory 28 is used by the processor 24 for the various filtering, detecting, identifying, suppressing, calculating, or other acts described for FIG. 1.

The instructions for implementing the processes, methods and/or techniques discussed above are provided on computer-readable storage media or memories, such as a cache, buffer, RAM, removable media, hard drive or other computer readable storage media, such as represented by the memory 28. Computer readable storage media include various types of volatile and nonvolatile storage media. The functions, acts or tasks illustrated in the figures or described herein are executed in response to one or more sets of instructions stored in or on computer readable storage media. The functions, acts or tasks are independent of the particular type of instructions set, storage media, processor or processing strategy and may be performed by software, hardware, integrated circuits, firmware, micro code and the like, operating alone or in combination. Likewise, processing strategies may include multi-processing, multitasking, parallel processing and the like. In one embodiment, the instructions are stored on a removable media device for reading by local or remote systems. In other embodiments, the instructions are stored in a remote location for transfer through a computer network or over telephone lines. In yet other embodiments, the instructions are stored within a given computer, CPU, GPU or system.

The display 27 is a CRT, LCD, plasma, projector, monitor, printer, touch screen, or other now known or later developed display device. The display 27 receives RGB or other color values and outputs an image. The image may be gray scale or color image. The image represents the region of the patient scanned by the beamformer and transducer 14.

While the invention has been described above by reference to various embodiments, it should be understood that many changes and modifications can be made without departing from the scope of the invention. It is therefore intended that the foregoing detailed description be regarded as illustrative rather than limiting, and that it be understood that it is the following claims, including all equivalents, that are intended to define the spirit and scope of this invention.

We claim:

1. A method for twinkle artifact suppression in color flow, the method comprising:
   acquiring color flow ultrasound data representing a patient;
   detecting a twinkle artifact represented in the color flow ultrasound data from the color flow ultrasound data, the detecting being a function of a decorrelation over time and spatial variance;
   suppressing the twinkle artifact in the color flow ultrasound data; and
   generating a color flow image with the color flow ultrasound data after the suppressing.

2. The method of claim 1 wherein acquiring comprises acquiring the color flow ultrasound data as velocity and power data.

3. The method of claim 1 wherein acquiring comprises scanning the patient with ultrasound and estimating velocities and powers from Doppler shifts.

4. The method of claim 1 wherein detecting comprises calculating the decorrelation over time for each of a plurality of locations of the patient from the color flow ultrasound data, identifying the locations with the decorrelation over a threshold, and calculating the spatial variance from the color flow ultrasound data for the identified locations and not for other locations.

5. The method of claim 1 wherein detecting comprises identifying each location of a plurality of locations of the patient for which the decorrelation over time is above a first threshold and the spatial variance is above a second threshold.

6. The method of claim 1 wherein the detecting further comprises detecting as a function of a correlation of power of the color flow ultrasound data.

7. The method of claim 6 wherein detecting comprises identifying each location of a plurality of locations of the patient for which the decorrelation over time is above a first threshold, the spatial variance is above a second threshold, and the correlation of power is above a third threshold.

8. The method of claim 1 wherein suppressing comprises suppressing as a function of a mask, the mask being a function of detected locations of the twinkling artifact.

9. The method of claim 1 wherein suppressing comprises assigning weights to locations as a function of the twinkle artifact, spatially filtering the weights, and weighting the color flow ultrasound data with the spatially filtered weights.

10. The method of claim 1 wherein generating the color flow image comprises generating a velocity image with fewer pixels mapped to a highest range of velocities.

11. A non-transitory computer readable storage medium having stored therein data representing instructions executable by a programmed processor for twinkle artifact suppression in color flow, the storage medium comprising instructions for:
    scanning a plurality of locations with ultrasound;
    estimating velocities and powers for each of the locations at different times;
    correlating the velocities and the powers from the different times for each of the locations;
    calculating spatial variance of at least some of the velocities for a first one of the different times;

altering the velocities and the powers for the locations based on results from the correlating and the spatial variance; and generating a velocity image with the velocities, including altered velocities resulting from the altering.

12. The non-transitory computer readable storage medium of claim 11 wherein correlating comprises calculating a difference between times.

13. The non-transitory computer readable storage medium of claim 11 wherein calculating the spatial variance comprises calculating for locations where results of the correlating are above a threshold.

14. The non-transitory computer readable storage medium of claim 11 wherein calculating the spatial variance comprises dividing a scan region into sections, each section including multiple of the locations, and calculating a spatial variance value for each of the sections.

15. The non-transitory computer readable storage medium of claim 14 wherein altering comprises altering the velocities for the locations with the spatial variance value above a first threshold and the results of the correlating below a second threshold.

16. The non-transitory computer readable storage medium of claim 11 wherein altering comprises reducing the velocities where the results and the spatial variance indicate an artifact to a greater extent than velocities where the results or the spatial variance do not indicate the artifact.

17. A system for twinkle artifact suppression in color flow, the system comprising:

a transducer and beamformer for scanning a scan region;

a Doppler estimator configured to estimate velocities and powers representing samples of the scan region at different times; and a processor configured to identify twinkling artifacts in the velocities and powers using spatial and temporal characteristics of the velocities and powers and to change the velocities and powers of the twinkling artifacts.

18. The system of claim 17 wherein the processor is configured to calculate the temporal characteristic as a decorrelation and the spatial characteristic as a spatial variance and configured to identify the twinkling artifacts where the decorrelation is above a first threshold and the spatial variance is above a second threshold.

19. The system of claim 17 wherein the processor is configured to change the velocities and powers as a function of a severity of the artifacts as indicated by the spatial and temporal characteristics.

20. The system of claim 17 wherein the processor is configured to change the velocities and the powers by reducing the velocities and the powers of the twinkling artifacts more than reducing of the velocities and the powers not of the twinkling artifacts.

* * * * *